United States Patent [19]

Honda et al.

[11] Patent Number: 5,112,613
[45] Date of Patent: May 12, 1992

[54] COSMETIC COMPOSITION

[75] Inventors: Shinkichi Honda, Kawasaki; Yoichiro Arai; Hiroshi Toida, both of Ibaraki, all of Japan

[73] Assignee: Kyowa Hakko Kogyo Co., Ltd., Tokyo, Japan

[21] Appl. No.: 644,567

[22] Filed: Jan. 23, 1991

[30] Foreign Application Priority Data

Jan. 27, 1990 [JP] Japan .................. 2-16484/90

[51] Int. Cl.$^5$ .............................. A61K 7/00
[52] U.S. Cl. ................... 424/400; 424/401; 514/844; 514/847
[58] Field of Search ............... 424/401; 514/844, 847

[56] References Cited

U.S. PATENT DOCUMENTS 3,932,622  1/1976  Friedman et al. ................ 514/943

FOREIGN PATENT DOCUMENTS 137275   6/1975  India .
1463975  2/1977  United Kingdom .

OTHER PUBLICATIONS

Folia Pharmacol. Japon, vol. 68, pp. 602–617 (1972), abstract only.
Basis and Clinic, vol. 8, No. 4, pp. 891–898 (1974) summary only.

Primary Examiner—Thurman K. Page
Assistant Examiner—Amy Hulina
Attorney, Agent, or Firm—Fitzpatrick, Cella, Harper & Scinto

[57] ABSTRACT

Disclosed is a cosmetic composition comprising N-acetylglutamine or a salt thereof.

The cosmetic composition of the present invention which is excellent in feel and stability is effective in retaining moisture in the stratum corneum.

4 Claims, No Drawings

COSMETIC COMPOSITION

BACKGROUND OF THE INVENTION

The present invention relates to a cosmetic composition comprising N-acetylglutamine.

Owing to external factors such as ultraviolet rays and dryness and physical factors such as aging, natural moisturizing factor (NMF) inherently held by the skin gradually decreases and thereby the skin becomes dry and rough. In order to provide a cosmetic composition effective for keeping the skin fresh and moist, use of amino acids and derivatives thereof which are the major components of NMF as a cosmetic base has been studied.

There are disclosed, for example, glutamine (IN Patent No. 137275), glutamic acid, acetylglutamic acid (U.S. Pat. No. 3,932,622), N-acylglutamic acid esters containing an acyl group having 7 to 21 carbon atoms (Japanese Published Unexamined Patent Application No. 67443/73), N-acyl-acidic amino acid esters containing an acyl group having 2 to 22 carbon atoms (Japanese Published Unexamined Patent Application No. 37839/79), N-lower acyl-acidic amino acid diesters containing an acyl group having 1 to 7 carbon atoms (Japanese Published Unexamined Patent Application No. 92237/74), N,N'-diacyl-basic amino acid esters containing an acyl group having 8 to 22 carbon atoms (Japanese Published Unexamined Patent Application No. 19138/76), etc. However, use of these substances as a cosmetic base has various drawbacks; for instance, they feel poor when they are applied to the skin, they irritate the skin, and an acetic acid odor is emanated during storage over a long period of time.

N-Acetylglutamine used in the present invention is an N-acetylated derivative of glutamine which is known to be excellent in heat stability compared to glutamine (Japanese Published Examined Patent Application No. 670/72).

In addition, the present substance is excellent in safety [KISO-TO-RINSHO (Basis and Clinic, Vol. 8, No. 4, Apr., 891–898 (1974)] and its aluminum salt has been used as an anti-ulcer agent for medical treatment [Folia Pharmacol. Japon, 68, 602-617 (1972)]. However, there has been no report on utilization of N-acetylglutamine as a cosmetic base.

SUMMARY OF THE INVENTION

The present invention provides a cosmetic composition comprising N-acetylglutamine or a salt thereof which is free from drawbacks involved in cosmetic bases heretofore used and is effective to enhance moisture retention in the stratum corneum. The present invention also provides a method of enhancing moisture retention in the stratum corneum by applying the cosmetic composition to the skin.

DETAILED DESCRIPTION OF THE INVENTION

N-Acetylglutamine may be prepared by any of the preparation methods such as fermentation and synthesis. For preparation by fermentation, for example, there are methods described in Japanese Published Unexamined Patent Application No. 41211/77 and Japanese Published Examined Patent Application No. 1994/82.

The cosmetic composition of the present invention comprises N-acetylglutamine, a salt thereof, or a mixture of N-acetylglutamine and a salt thereof, and a cosmetically acceptable component.

Examples of the salts of N-acetylglutamine include salts with alkali metals such as sodium, potassium and lithium, salts with alkaline earth metals such as calcium and magnesium, ammonium salts, and salts with amines such as monoethanolamine, triethanolamine and triisopropanolamine. These alkaline components may be used singly or in combination.

These salts of N-acetylglutamine can be prepared from N-acetylglutamine in a conventional manner.

N-Acetylglutamine and/or salts thereof are employed in the composition in an amount of 0.001 to 10.0 w/w %, preferably 0.005 to 5.0 w/w %.

The cosmetically acceptable components are fats and oils, hydrocarbons, waxes, fatty acids, synthetic esters, alcohols, surfactants, thickeners, moisturizers, preservatives, fragrances, pigments and chemicals which are conventionally used in cosmetics.

Examples of the fats and oils include jojoba oil, castor oil, olive oil, soybean oil, coconut oil, palm oil, cacao butter, mink oil, turtle oil and coconut oil fatty acid diethanolamide.

Examples of the hydrocarbons include liquid paraffin, vaseline, microcrystalline wax and squalane Examples of the waxes include beeswax, lanoline, carnauba wax and candelilla wax.

Examples of the fatty acids include myristic acid, palmitic acid, stearic acid, oleic acid and isostearic acid.

Examples of the synthetic esters include isopropyl myristate, isopropyl palmitate, butyl oleate, myristyl myristate, octyldecyl myristate, propylene glycol monostearate, myristyl lactate, isostearyl malate, glycerine monostearate and distearyldimethyl ammonium chloride.

The fats and oils, hydrocarbons, waxes, fatty acids and synthetic esters are usually employed in the composition in an amount of 0.1 to 30 w/w % collectively.

Examples of the alcohols include ethanol, 1,3-butylene glycol, propylene glycol, lauryl alcohol, cetanol, stearyl alcohol and oleyl alcohol The alcohols are employed in the composition in an amount of 0.1 to 25 w/w%.

Examples of the surfactants include polyoxyethylene-hardened castor oil, sodium lauryl sulfate, polyoxyethyleneglyceryl pyroglutamate isostearate, sodium alkylbenzene sulfonate, polyoxyethylene (10) stearyl ether, dialkyl sulfosuccinate, cetyl pyridinium bromide, n-octadecyl trimethylammonium chloride, monoalkyl phosphate, N-acylglutamic acid, sucrose fatty acid ester, polyoxyethylene (20) sorbitan monostearate, sodium polyoxyethylene lauryl ether sulfate and polyoxyethylene-reduced lanoline.

The surfactants are usually employed in the composition in an amount of 0.1 to 5 w/w %, and in the case of a shampoo, in an amount of 0.1 to 40 w/w %.

Examples of the thickeners include carboxyvinyl polymer, methylpolysiloxane, dextran, carboxymethyl cellulose, carrageenan and hydroxypropyl methyl cellulose. The thickeners are usually employed in the composition in an amount of 0.01 to 0.5 w/w %.

Examples of the moisturizers include glycerine, propylene glycol, 1,3-butylene glycol, pyrrolidonecarboxylic acid, lactic acid and hyaluronic acid. The moisturizers are employed in the composition in an amount of 0.01 to 25 w/w %.

Examples of the preservatives include benzoic acid, salicylic acid, dehydroacetic acid or salts thereof, phenols such as p-oxybenzoic acid ester, triclosan and halocarban. The preservatives are employed in the composition in an amount of 0.01 to 0.3 w/w %.

Any fragrance may be used so long as it is conventionally used in cosmetics.

Examples of the pigments include iron oxide, titanium dioxide, zinc oxide, kaolin and talc. The pigments are employed in the composition in an amount of 0.01 to 1 w/w %.

Examples of the chemicals include wheat germ oil, vitamin E, vitamin A, vitamin B2, magnesium ascorbic acid-2-phosphate, D-pantothenyl alcohol, dipotassium glycyrrhizinate and glutathione. The chemicals are employed in the composition in an amount of 0.01 to 5 w/w %.

The cosmetic composition may take any form of soluble system, emulsion type, dispersion system, and the like.

As cosmetic preparations of the present invention, there are, for example, skin care products such as a lotion, an emulsion, a cream, soap and pack; makeup cosmetics such as a lipstick, foundation, eye shadow and eyeliner; and hair care products such as a shampoo and a rinse.

The cosmetic composition of the present invention which is excellent in feel and stability is effective in retaining moisture in the stratum corneum.

The present invention is described below by referring to examples and test examples. In the examples, the unit in the compositions is w/w %.

EXAMPLE 1

Lotion (I) having the following composition was prepared.

| Composition 1: | |
|---|---|
| (1) N-Acetylglutamine | 0.5 |
| (2) Sodium hydroxide | 0.1 |
| (3) 1,3-Butylene glycol | 5.0 |
| (4) Ethanol | 7.0 |
| (5) Methyl p-oxybenzoate | 0.1 |
| (6) Polyoxyethylene-hardened castor oil (60 E.O.) | 0.3 |
| (7) Fragrance | 0.03 |
| (8) Purified water | 86.97 |

Method of preparation:

A homogeneous solution of the ingredients (4), (5), (6) and (7) was added to a homogeneous solution of the ingredients (1), (2), (3) and (8) to make a lotion.

EXAMPLE 2

Lotion (II) having the following composition was prepared.

| Composition 2: | |
|---|---|
| (1) N-Acetylglutamine | 0.5 |
| (2) Triethanolamine | 0.6 |
| (3) Carboxyvinyl polymer | 0.18 |
| (4) 1,3-Butylene glycol | 8.0 |
| (5) Glycerine | 8.0 |
| (6) Ethanol | 1.0 |
| (7) Methyl p-oxybenzoate | 0.1 |
| (8) Wheat germ oil | 0.1 |
| (9) Polyoxyethylene glyceryl pyroglutamate isostearate (25 E.O.) | 1.2 |
| (10) Fragrance | 0.05 |

| -continued | |
|---|---|
| Composition 2: | |
| (11) Purified water | 80.27 |

Method of preparation:

A homogeneous solution of the ingredients (6), (7), (8), (9) and (10) was added to a homogeneous solution of the ingredients (1), (2), (3), (4), (5) and (11) to make a lotion.

EXAMPLE 3

An emulsion having the following composition was prepared.

| Composition 3: | |
|---|---|
| (1) N-Acetylglutamine | 0.5 |
| (2) 1,3-Butylene glycol | 4.0 |
| (3) Glycerine | 2.0 |
| (4) Triethanolamine | 0.4 |
| (5) Squalane | 4.5 |
| (6) Isopropyl myristate | 2.5 |
| (7) Methyl polysiloxane | 0.5 |
| (8) Glycerine monostearate | 1.5 |
| (9) Polyoxyethylene (10) stearyl ether | 3.0 |
| (10) Methyl p-oxybenzoate | 0.2 |
| (11) Fragrance | 0.05 |
| (12) Purified water | 80.85 |

Method of preparation:

The ingredients (1), (2), (3), (4) and (12) and a half of the ingredient (10) were heated to make a solution. The ingredients (5), (6), (7), (8), (9) and (11) and the remaining half of the ingredient (10) were heated to make a solution. The resulting solutions were mixed and the mixture was cooled to make an emulsion.

EXAMPLE 4

A cream having the following composition was prepared.

| Composition 4: | |
|---|---|
| (1) Squalane | 8.0 |
| (2) Isopropyl myristate | 5.0 |
| (3) Wheat germ oil | 5.0 |
| (4) Stearic acid | 4.0 |
| (5) Glycerine monostearate | 3.0 |
| (6) Cetanol | 2.0 |
| (7) Beeswax | 2.0 |
| (8) Triethanolamine | 1.3 |
| (9) Methyl p-oxybenzoate | 0.1 |
| (10) N-Acetylglutamine | 0.3 |
| (11) 1,3-Butylene glycol | 5.0 |
| (12) Fragrance | 0.07 |
| (13) Purified water | 64.23 |

Method of preparation:

(i) The ingredients (1) through (7) were heated to 75° C. to make a homogeneous mixture.

(ii) The ingredients (8) through (11) and (13) were heated to 75° C. to make a homogeneous mixture.

(iii) The mixture obtained in (ii) was added to the mixture obtained in (i) with stirring to make a homogeneous mixture.

(iv) The ingredient (12) was added to the mixture obtained in (iii) with stirring and the resulting mixture was cooled to make a cream.

EXAMPLE 5

A shampoo having the following composition was prepared.

| Composition 5: | | |
|---|---|---|
| (1) | Sodium polyoxyethylene lauryl ether sulfate | 30.0 |
| (2) | Coconut oil fatty acid diethanolamide | 5.0 |
| (3) | Polyoxyethylene-reduced lanoline (15 E.O.) | 3.0 |
| (4) | Jojoba oil | 0.3 |
| (5) | N-Acetylglutamine | 0.3 |
| (6) | Sodium hydroxide | 0.065 |
| (7) | Fragrance | 0.20 |
| (8) | Pigment (Blue No. 1) | 0.0005 |
| (9) | Purified water | 61.1345 |

Method of preparation:

(i) The ingredients (1) through (4) were heated to 70° C. to make a homogeneous mixture.

(ii) The ingredients (5), (6), (8) and (9) were heated to 70° C. and added to the mixture obtained in (i) to make a homogeneous mixture.

(iii) The ingredient (7) was added to the mixture obtained in (ii) with stirring and the resulting mixture was cooled to make a shampoo.

EXAMPLE 6

A rinse having the following composition was prepared.

| Composition 6: | | |
|---|---|---|
| (1) | Distearyl dimethyl ammonium chloride | 0.5 |
| (2) | Cetanol | 0.5 |
| (3) | Propylene glycol | 5.0 |
| (4) | N-Acetylglutamine | 0.3 |
| (5) | Triethanolamine | 0.3 |
| (6) | Hydroxypropylmethyl cellulose | 0.05 |
| (7) | Fragrance | 0.20 |
| (8) | Purified water | 93.15 |

Method of preparation:

(i) The ingredients (1), (2) and (3) were heated to 75° C. to make a homogeneous mixture.

(ii) The ingredients (4), (5), (6) and (8) were heated to 75° C. to make a homogeneous mixture.

(iii) The mixture obtained in (ii) was added to the mixture obtained in (i) with stirring.

(iv) The ingredient (7) was added to the mixture obtained in (iii) with stirring and the resulting mixture was cooled to make a rinse.

TEST EXAMPLE 1

In vivo test on moisture load in the stratum corneum

A 25 year old female volunteer with a mildly dry skin was made the subject of the test. After her face was washed, each of the following samples was applied to the face. The electric conductivity of the skin after the application was determined at 10-30 second intervals of time, using a 3.5 MHz high frequency conductivity measuring device [SKIN SURFACE HYDROMETER SKICON-200 (manufactured by I.B.S.)].

The moisture content in the stratum corneum of the skin was determined by the method of Tagami, et al. [JOURNAL OF INVESTIGATIVE DERMATOLOGY, 78, 425 (1982)].

Sample (1): 0.5 w/w % aqueous solution of N-acetylglutamine

Sample (2): 10 w/w % aqueous solution of 1,3-butylene glycol

Sample (3): 1.0 w/w % aqueous solution of L-serine

The results are shown in Table 1.

TABLE 1

| Sample | Before Application | Upon Application | Conductivity ($\mu$) (sec.) | | | | | | |
|---|---|---|---|---|---|---|---|---|---|
| | | | 10 | 20 | 30 | 40 | 60 | 90 | 120 |
| (1) | 35 | 682 | 608 | 445 | 338 | 256 | 210 | 155 | 141 |
| (2) | 35 | 581 | 420 | 270 | 143 | 112 | 80 | 44 | 31 |
| (3) | 35 | 410 | 230 | 149 | 72 | 60 | 48 | 30 | 28 |

The conductivity becomes higher as the moisture content in the stratum corneum increases [Fragrance Journal, Extra Edition, 5, 383–386 (1984)]. Therefore, it can be seen that N-acetylglutamine is excellent in retaining moisture over a long period of time compared to other moisturizers.

TEST EXAMPLE 2

Organoleptic Test

The lotion obtained in Example 1 and a lotion containing no N-acetylglutamine (the same composition as Composition 1 except for N-acetylglutamine) were evaluated by 25 experts in respect of (a) smoothness of skin, (b) moistness of skin, (c) durability of moistness of skin and (d) softness of skin, according to the following scoring method.

The test lotion was applied twice a day (morning and evening) for consecutive one month. The results are shown in Table 2.

Almost the same results were obtained with the salts of N-acetylglutamine.

TABLE 2

| | | Lotion of the Invention | | | Conventional Lotion (Comparative Example) | | |
|---|---|---|---|---|---|---|---|
| | | Very Good | Good | Ordinary | Very Good | Good | Ordinary |
| (a) | Smoothness of skin | 20 | 3 | 2 | 2 | 7 | 16 |
| (b) | Moistness of skin | 18 | 5 | 2 | 3 | 3 | 19 |
| (c) | Durability of moistness of skin | 17 | 5 | 3 | 0 | 2 | 23 |
| (d) | Softness of skin | 19 | 2 | 4 | 3 | 6 | 16 |

(Numerals in the table indicate the number of persons.)

TEST EXAMPLE 3

Stability Test

The stability of N-acetylglutamine and glutamine in aqueous solution was examined by HPLC (UV absorption at a wavelength of 220 nm).

Samples (pH 7.0, 40° C.)

Sample (1): 1.0% aqueous solution of N-acetylglutamine

Sample (2): 1.0% aqueous solution of glutamine

The results are shown in Table 3.

TABLE 3

| Sample | Time (Day) | Residual Rate in Aqueous Solution (%) |
|---|---|---|
| (1) | 1 | 100 |
|  | 2 | 100 |
|  | 5 | 100 |
|  | 7 | 100 |
| (2) | 1 | 94.0 |
|  | 2 | 90.2 |
|  | 5 | 68.0 |
|  | 7 | 58.6 |

What is claimed is:

1. A cosmetic composition comprising 0.001–10.0 w/w % of N-acetylglutamine or a salt thereof and a cosmetically acceptable component selected from the group consisting of fats and oils, hydrocarbons, waxes, fatty acids, synthetic esters, alcohols, surfactants, thickeners, moisturizers, preservatives, and fragrances.

2. A cosmetic composition according to claim 1 which comprises:
   0.001–10.0 w/w % of N-acetylglutamine or the salt thereof;
   0.1–30 w/w % of an fat and oil, a hydrocarbon, a wax, a fatty acid and a synthetic ester collectively;
   0.1–25 w/w % of an alcohol;
   0.1–40 w/w % of a surfactant;
   0.01–0.5 w/w % of a thickener;
   0.01–25 w/w % of a moisturizer;
   0.01–0.3 w/w % of a preservative;
   0.01–1 w/w % of a pigment;
   0.01–5 w/w % of a chemical;
   a fragrance;
   water;
   and a cosmetically acceptable carrier.

3. A method of enhancing moisture retention in the stratum corneum, which comprises the step of applying to the skin a cosmetic composition of claim 1 comprising 0.001–10.0 w/w % of N-acetylglutamine or a salt thereof.

4. A cosmetic composition according to claim 2, which comprises 0.005–5.0 w/w % of N-acetylglutamine or salts thereof.

* * * * *

UNITED STATES PATENT AND TRADEMARK OFFICE
CERTIFICATE OF CORRECTION

Page 1 of 2

PATENT NO. : 5,112,613

DATED : May 12, 1992

INVENTOR(S) : SHINKICHI HONDA, ET AL.

It is certified that error appears in the above-identified patent and that said Letters Patent is hereby corrected as shown below:

COLUMN 1

Line 61, "N-Acetylglutamine" should read --N-acetylglutamine--.

COLUMN 2

Line 12, "N-Acetylglutamine" should read --N-acetylglutamine--.
Line 24, "of-the" should read --of the--.
Line 25, "squalane" should read --squalane.--.
Line 41, "alcohol The" should read --alcohol. The--.

COLUMN 3

Line 11, "vitamin B2," should read --vitamin $B_2$,--.

COLUMN 5

Line 64, "25 year old" should read --25-year-old--.

COLUMN 6

TABLE 1, "Conductivity (µ )" should read --Conductivity (µ ℧)--.

UNITED STATES PATENT AND TRADEMARK OFFICE
CERTIFICATE OF CORRECTION

PATENT NO. : 5,112,613

DATED : May 12, 1992

INVENTOR(S) : SHINKICHI HONDA, ET AL.

It is certified that error appears in the above-identified patent and that said Letters Patent is hereby corrected as shown below:

COLUMN 8

Line 5, "an" should read --a--.
Line 13 should be deleted.

Signed and Sealed this

Seventh Day of September, 1993

Attest:

BRUCE LEHMAN

*Attesting Officer*  *Commissioner of Patents and Trademarks*